(12) United States Patent
Chen et al.

(10) Patent No.: US 11,763,944 B2
(45) Date of Patent: Sep. 19, 2023

(54) SYSTEM AND METHOD FOR CLINICAL DECISION SUPPORT SYSTEM WITH INQUIRY BASED ON REINFORCEMENT LEARNING

(71) Applicant: TENCENT AMERICA LLC, Palo Alto, CA (US)

(72) Inventors: Xiaozhong Chen, Cedarburg, WI (US); Kun Wang, San Jose, CA (US); Nan Du, Santa Clara, CA (US); Min Tu, Cupertino, CA (US); Shangqing Zhang, San Jose, CA (US); Yusheng Xie, Mountain View, CA (US); Wei Fan, New York, NY (US)

(73) Assignee: TENCENT AMERICA LLC, Palo Alto, CA (US)

(*) Notice: Subject to any disclaimer, the term of this patent is extended or adjusted under 35 U.S.C. 154(b) by 128 days.

(21) Appl. No.: 16/409,293

(22) Filed: May 10, 2019

(65) Prior Publication Data

US 2020/0357515 A1    Nov. 12, 2020

(51) Int. Cl.
*G16H 50/20*    (2018.01)
*G16H 10/60*    (2018.01)
*G06N 20/00*    (2019.01)

(52) U.S. Cl.
CPC ............. *G16H 50/20* (2018.01); *G06N 20/00* (2019.01); *G16H 10/60* (2018.01)

(58) Field of Classification Search
CPC ......... G16H 10/60; G16H 50/20; G06N 20/00
See application file for complete search history.

(56) References Cited

U.S. PATENT DOCUMENTS

| 5,660,176 A * | 8/1997 | Iliff ................. G16H 40/67 706/924 |
| 10,395,772 B1 * | 8/2019 | Lucas ............. G06K 9/6262 |
| 2018/0025112 A1 * | 1/2018 | Takeda ............ G06K 9/00 705/2 |
| 2018/0218126 A1 * | 8/2018 | Salazar ........... G16H 50/30 |

(Continued)

FOREIGN PATENT DOCUMENTS

| AU | 2019322953 B2 * | 8/2021 | .......... G06N 3/0427 |
| WO | WO-2012122196 A2 * | 9/2012 | ............ G16H 50/20 |

OTHER PUBLICATIONS

A. Dehghan, J. A. Keane and G. Nenadic, "Challenges in Clinical Named Entity Recognition for Decision Support," 2013 IEEE International Conference on Systems, Man, and Cybernetics, Manchester, 2013, pp. 947-951. (Year: 2013).*

(Continued)

*Primary Examiner* — Mamon Obeid
*Assistant Examiner* — Chance L Smith
(74) *Attorney, Agent, or Firm* — Sughrue Mion, PLLC

(57) ABSTRACT

A method and apparatus include receiving, by a device, medical information associated with a user. Inquiry information is determined based on the medical information associated with the user and a reinforcement learning model. The inquiry information is provided to permit response information to be received. The response information is received based on providing the inquiry information. Diagnosis information is determined based on the medical information and the response information using a machine learning model. The diagnosis information is provided to a set of devices via a network.

17 Claims, 4 Drawing Sheets

(56) References Cited

U.S. PATENT DOCUMENTS

| | | | | |
|---|---|---|---|---|
| 2019/0311807 A1* | 10/2019 | Kannan | ................ | G16H 50/70 |
| 2019/0311814 A1* | 10/2019 | Kannan | ................ | G16H 10/60 |
| 2020/0097718 A1* | 3/2020 | Schafer | ............... | G06K 9/6256 |
| 2020/0111578 A1* | 4/2020 | Koblick | ................ | G06N 20/00 |
| 2021/0110895 A1* | 4/2021 | Shriberg | ............... | G06F 40/20 |

OTHER PUBLICATIONS

Zhang Y, Jiang M, Wang J, Xu H. Semantic Role Labeling of Clinical Text: Comparing Syntactic Parsers and Features. AMIA Annu Symp Proc. 2017;2016:1283-1292. Published Feb. 10, 2017. (Year: 2017).*

Peter Garrett and Joshua Seidman. "EMR vs EHR—What is the Difference?" The Office of the National Coordinator for Health Information Technology. https://www.healthit.gov/buzz-blog/electronic-health-and-medical-records/emr-vs-ehr-difference (Year: 2011).*

McSherry, David. "Conversational case-based reasoning in medical decision making." Artificial Intelligence in Medicine 52.2 (2011): 59-66. (Year: 2011).*

* cited by examiner

300

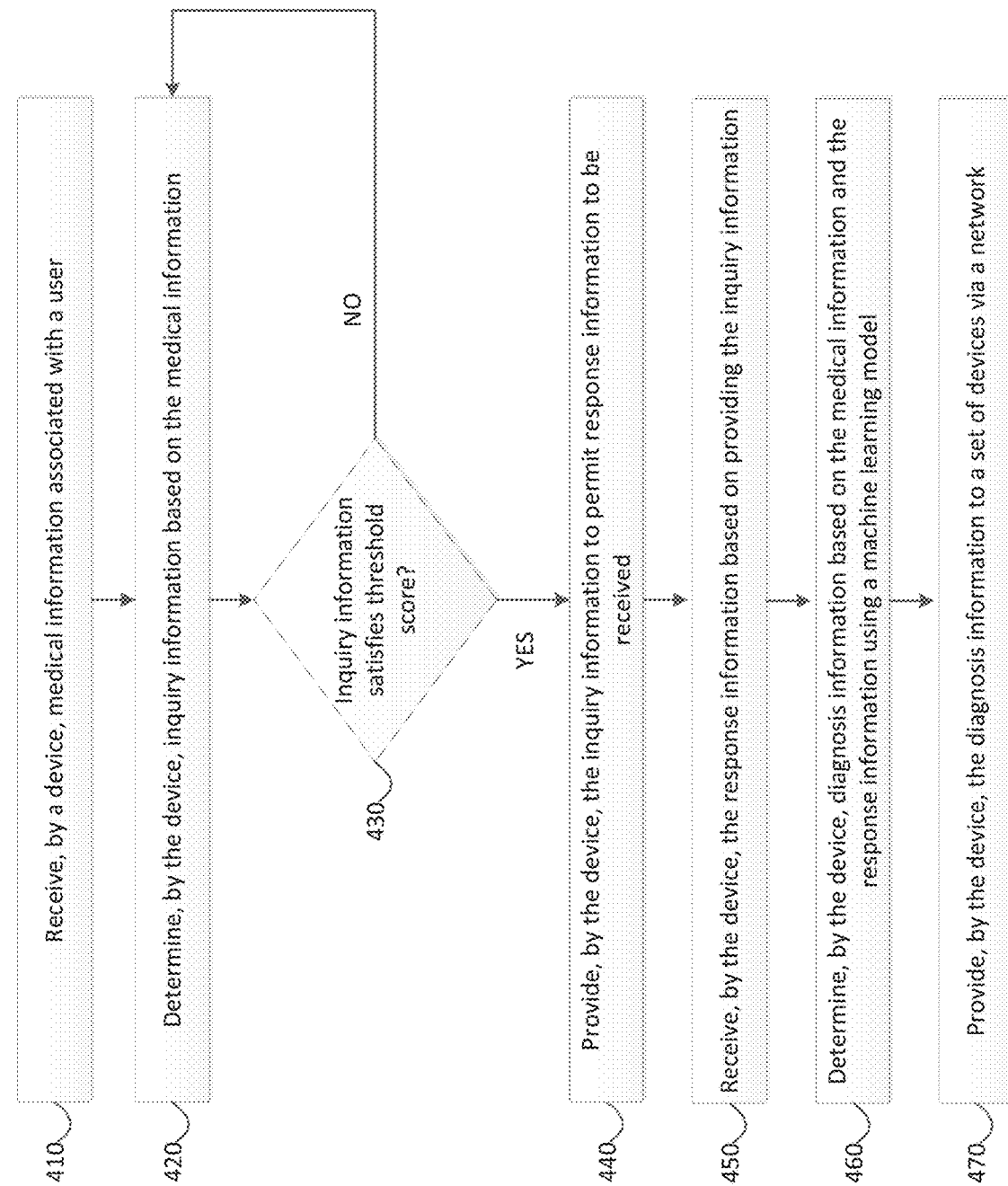

SYSTEM AND METHOD FOR CLINICAL DECISION SUPPORT SYSTEM WITH INQUIRY BASED ON REINFORCEMENT LEARNING

BACKGROUND

With the introduction of electronic health records, additional digital data has become available for analysis and decision support. Thus, when doctors are diagnosing a patient, they need to consider and evaluate a large range of various and voluminous data, which makes clinical decision increasingly complex. Machine learning-based clinical decision support systems can provide a solution to such data challenges. The present disclosure provides a decision support system with which physicians' decisions are directly predicted. Concretely, the model assigns higher probabilities to decisions that it presumes are crucial in evaluating a final diagnosed disease. Thus, the system can provide physicians with rational recommendations.

SUMMARY

According to an aspect of the disclosure, a method includes receiving, by a device, medical information associated with a user; determining, by the device, inquiry information based on the medical information associated with the user and a reinforcement learning model; providing, by the device, the inquiry information to permit response information to be received; receiving, by the device, the response information based on providing the inquiry information; determining, by the device, diagnosis information based on the medical information and the response information using a machine learning model; and providing, by the device, the diagnosis information to a set of devices via a network.

According to an aspect of the disclosure, a device comprises at least one memory configured to store program code; and at least one processor configured to read the program code and operate as instructed by the program code, the program code including: first receiving code configured to cause the at least one processor to receive medical information associated with a user; first determining code configured to cause the at least one processor to determine inquiry information based on the medical information associated with the user and a reinforcement learning model; providing code configured to cause the at least one processor to provide the inquiry information to permit response information to be received; second receiving code configured to cause the at least one processor to receive the response information based on providing the inquiry information; second determining code configured to cause the at least one processor to determine diagnosis information based on the medical information and the response information using a machine learning model; and providing code configured to cause the at least one processor to provide the diagnosis information to a set of devices via a network.

According to an aspect of the disclosure, a non-transitory computer-readable medium stores instructions, the instructions comprising: one or more instructions that, when executed by one or more processors of a device, cause the one or more processors to: receive medical information associated with a user; determine inquiry information based on the medical information associated with the user and a reinforcement learning model; provide the inquiry information to permit response information to be received; receive the response information based on providing the inquiry information; determine diagnosis information based on the medical information and the response information using a machine learning model; and provide the diagnosis information to a set of devices via a network.

BRIEF DESCRIPTION OF THE DRAWINGS

FIG. 4 is a flow chart of an example process for determining diagnosis information using a reinforcement learning model.

DETAILED DESCRIPTION

To improve medication safety and efficiency, several clinical decision support systems have been developed and implemented. Studies with these systems have shown promising improvements of doctors' performance and a reduction of medication errors. To reduce the risk of human error as well as the workload of medical staff, the application of medical software has long been suggested as a possible tool. To prevent medication errors, the application should be designed as an automated database with historical and current medical records of a patient, as well as other key information, including all prescription and personal allergic reaction documents to prevent any inappropriate prescriptions and provide warnings. In addition, computer assisted diagnosis software is used to increase the accuracy of diagnosis and decrease the time that is needed for decision making.

One of the major difficulties of clinical decision support systems is the long-term predictability. At the early stages of many diseases, there are symptoms that may be very common such as fever, rush, etc. However, even some general clinical tests cannot find the clues. In such cases, some existing clinical decision support systems are likely to provide a suggestion that corresponds to a common and trivial disease, which leads to a misdiagnosis.

Current clinical decision support systems usually lack forward-looking ability, and can only passively receive information from users and only make suggestions based on known observations. However, due to negligence, some informative features may not be uncovered. Thus, a reliable clinical decision support system should initiatively guide a user to determine as much informative information as possible. The present disclosure provides new techniques including reinforcement Learning and heterogonous learning to improve clinical decision support systems' long-term predictability.

The present disclosure provides accurate clinical suggestions using reinforcement learning techniques to determine latent and unobserved clinical information. For example, the present disclosure utilizes a reinforcement learning-based algorithm that can determine, based on current observed clinical findings, which information should be confirmed from the patient to provide the most information and most valuable suggestions. A reward function in the reinforcement learning module is designed based on different clinical data format including electronic medical record (EMR)/electronic health record (EHR), rules, and/or other types of knowledge bases. Therefore, the present disclosure can be widely applied to various types of clinical suggestion tasks.

Figure 1:
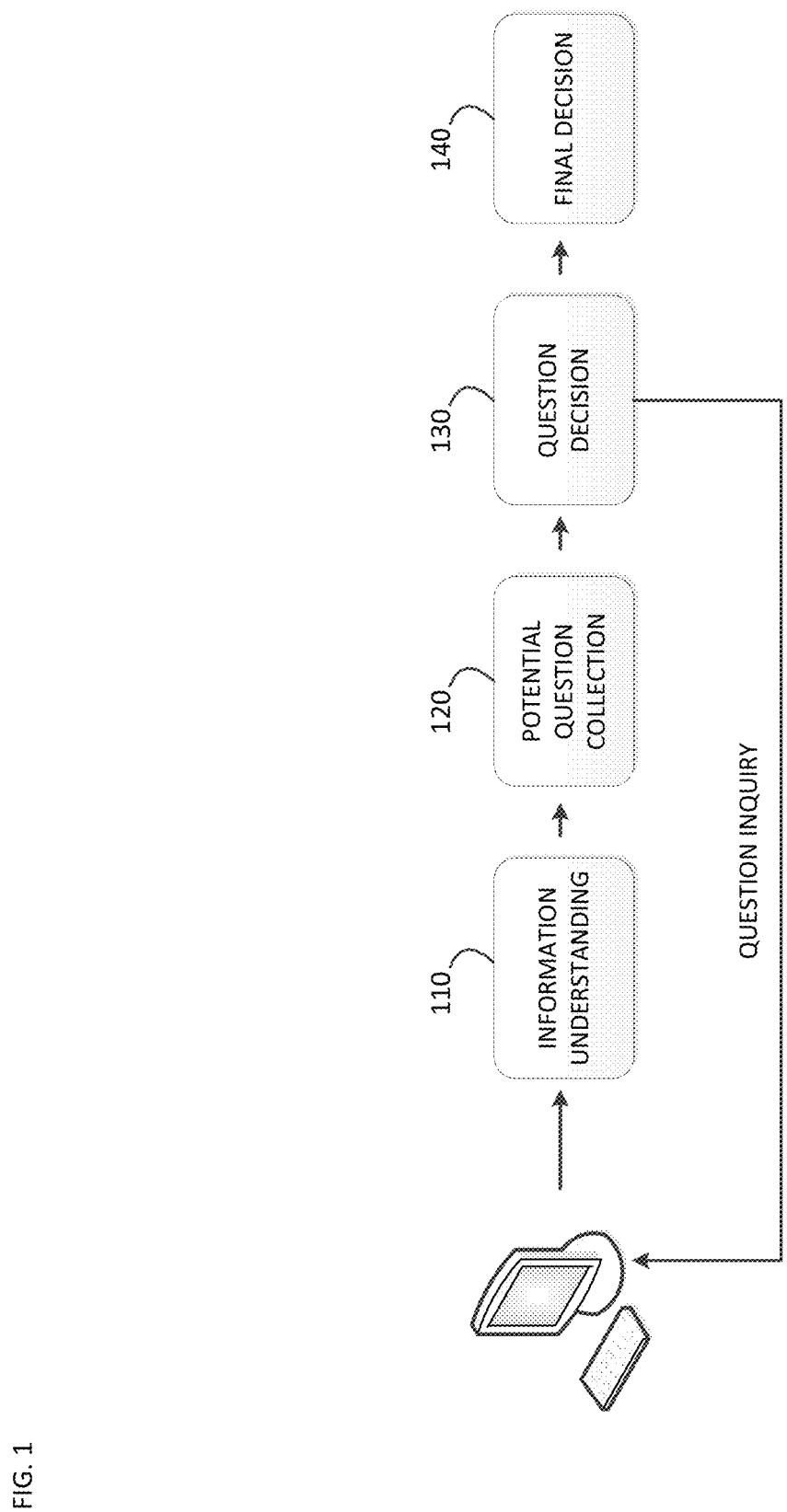
FIG. 1 is a diagram of an overview of an example implementation described herein.

FIG. 1 is a diagram of an overview of an embodiment described herein. As shown in FIG. 1, and by reference number 110, an information understanding module may detect valuable information from clinical data in a text format. As an example, in a patient's medical description, especially in their previous disease history and symptoms, there are some important hints for a heart abnormities analysis. Therefore, the information understanding module is determines this informative information from medical record information. The information understanding module includes components such as named entity recognition (NER), semantic role labeling, and/or the like.

As further shown in FIG. 1, and by reference number 120, a potential question collection module is designed for extracting appropriate questions that doctors can interact with the patients, or take actions based on current known clinical observations. As examples, these questions may be questions about current illnesses, illness history, medicine history for the patient, a test result the doctor should evaluate from the patient, and/or the like. The questions may cover any actions or information in a clinical diagnosis environment.

As further shown in FIG. 1, and by reference number 130, after collecting the potential questions, a question decision module is used to estimate each question's importance, and based on them, make the decision regarding which question to ask. This estimation is made based on reinforcement learning in which a reward function, that is trained on a large volume of EMR/HER data or defined based on a knowledge base or rule, scores each question's importance. As an example, if a question which is unclear may be due to a terrible consequence such as death or sequela, its importance is high. Finally, by considering the known information, the dialogue influence and input from the medical professional, the system decides the final question to ask.

As further shown in FIG. 1, and by reference number 140, based on the known observations which are learned from the text or determined during the inquiry, the system uses a machine learning module to provide the final decision to the user.

The proposed training framework is designed as an end-to-end framework. As compared to other clinical decision support systems, the present framework can learn and extract information from both raw description and collected information via inquiry. In this way, instead of passively waiting for input such as in convention clinical decision support systems, the present disclosure determines a final decision via both raw and inquiry-based information. Moreover, the present framework can collect different types of clinical questions (e.g., current illness, family history, previous illness, etc.) and provide different types of suggestions (e.g., test, exam, drug recommendations, etc.) which could provide comprehensive information for the users. Last, the present framework can transmit a message in a standardized format over a network to all medical personnel and/or other users that have access to the patient's information. In this way, all users can quickly be notified of any changes without having to manually search for such information.

In other implementations, the information understanding module utilizes various machine learning algorithms such as recurrent neural networks (RNN), convolutional neural network (CNN), support vector machine (SVM), and/or the like. Further, the reward function in the question decision module is designed based on EHR/EMR, knowledge base, rules, and/or the like.

Further, the framework is designed as an end-to-end procedure and the whole framework is optimized and altered simultaneously. In an alternative embodiment, the framework includes a step-by-step training procedure, in which the modules can be trained separately.

Figure 2:
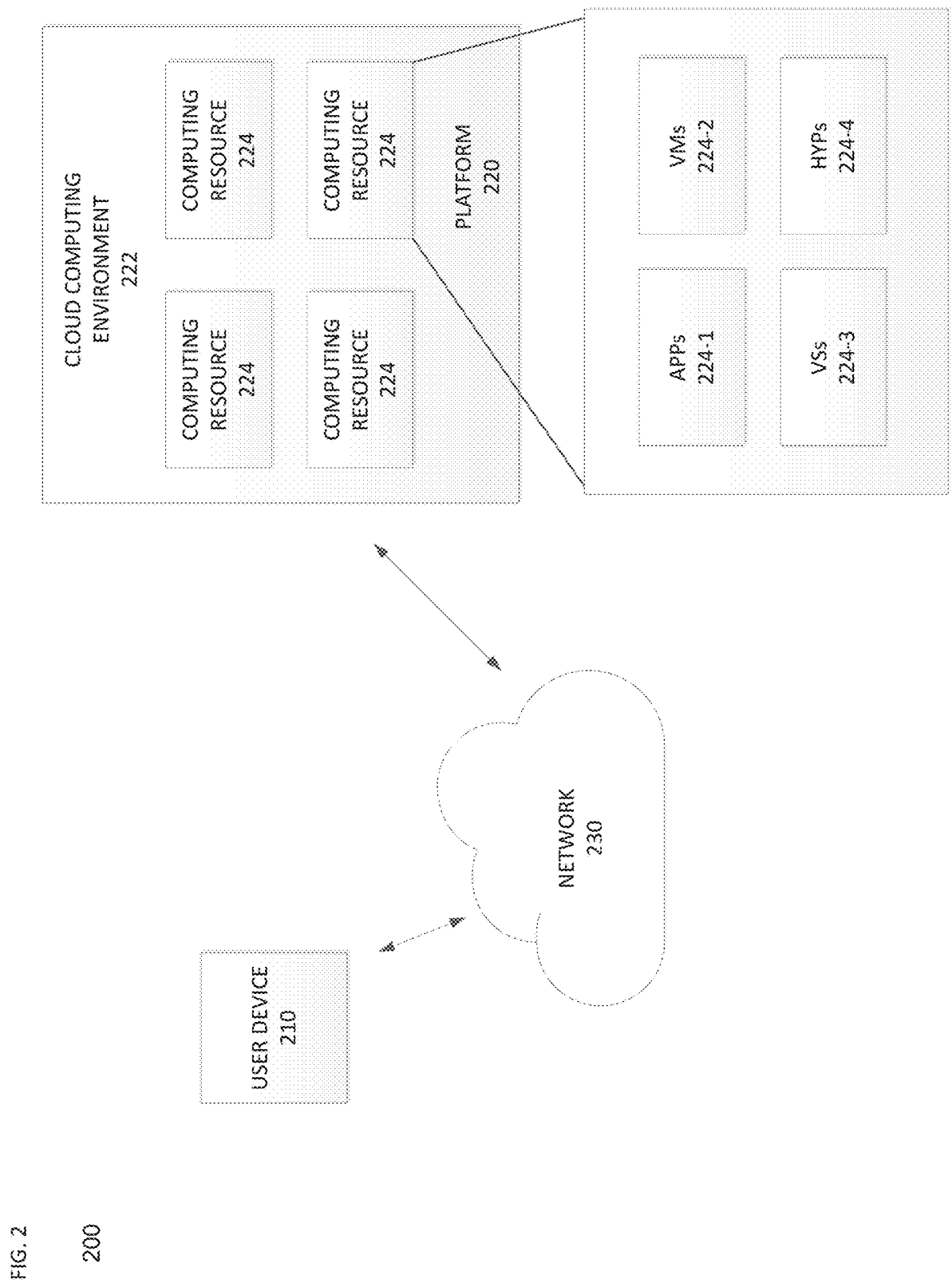
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a user device 210, a platform 220, and a network 230. Devices of environment 200 may interconnect via wired connections, wireless connections, or a combination of wired and wireless connections.

User device 210 includes one or more devices capable of receiving, generating, storing, processing, and/or providing information associated with platform 220. For example, user device 210 may include a computing device (e.g., a desktop computer, a laptop computer, a tablet computer, a handheld computer, a smart speaker, a server, etc.), a mobile phone (e.g., a smart phone, a radiotelephone, etc.), a wearable device (e.g., a pair of smart glasses or a smart watch), or a similar device. In some implementations, user device 210 may receive information from and/or transmit information to platform 220.

Platform 220 includes one or more devices capable of determining diagnosis information using a reinforcement learning model, as described elsewhere herein. In some implementations, platform 220 may include a cloud server or a group of cloud servers. In some implementations, platform 220 may be designed to be modular such that certain software components may be swapped in or out depending on a particular need. As such, platform 220 may be easily and/or quickly reconfigured for different uses.

In some implementations, as shown, platform 220 may be hosted in cloud computing environment 222. Notably, while implementations described herein describe platform 220 as being hosted in cloud computing environment 222, in some implementations, platform 220 is not be cloud-based (i.e., may be implemented outside of a cloud computing environment) or may be partially cloud-based.

Cloud computing environment 222 includes an environment that hosts platform 220. Cloud computing environment 222 may provide computation, software, data access, storage, etc. services that do not require end-user (e.g., user device 210) knowledge of a physical location and configuration of system(s) and/or device(s) that hosts platform 220. As shown, cloud computing environment 222 may include a group of computing resources 224 (referred to collectively as "computing resources 224" and individually as "computing resource 224").

Computing resource 224 includes one or more personal computers, workstation computers, server devices, or other types of computation and/or communication devices. In some implementations, computing resource 224 may host platform 220. The cloud resources may include compute instances executing in computing resource 224, storage devices provided in computing resource 224, data transfer devices provided by computing resource 224, etc. In some implementations, computing resource 224 may communicate with other computing resources 224 via wired connections, wireless connections, or a combination of wired and wireless connections.

As further shown in FIG. 2, computing resource 224 includes a group of cloud resources, such as one or more applications ("APPs") 224-1, one or more virtual machines ("VMs") 224-2, virtualized storage ("VSs") 224-3, one or more hypervisors ("HYPs") 224-4, or the like.

Application 224-1 includes one or more software applications that may be provided to or accessed by user device 210 and/or sensor device 220. Application 224-1 may eliminate a need to install and execute the software applications on user device 210. For example, application 224-1 may include software associated with platform 220 and/or any other software capable of being provided via cloud computing environment 222. In some implementations, one application 224-1 may send/receive information to/from one or more other applications 224-1, via virtual machine 224-2.

Virtual machine 224-2 includes a software implementation of a machine (e.g., a computer) that executes programs like a physical machine. Virtual machine 224-2 may be either a system virtual machine or a process virtual machine, depending upon use and degree of correspondence to any real machine by virtual machine 224-2. A system virtual machine may provide a complete system platform that supports execution of a complete operating system ("OS"). A process virtual machine may execute a single program, and may support a single process. In some implementations, virtual machine 224-2 may execute on behalf of a user (e.g., user device 210), and may manage infrastructure of cloud computing environment 222, such as data management, synchronization, or long-duration data transfers.

Virtualized storage 224-3 includes one or more storage systems and/or one or more devices that use virtualization techniques within the storage systems or devices of computing resource 224. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 224-4 may provide hardware virtualization techniques that allow multiple operating systems (e.g., "guest operating systems") to execute concurrently on a host computer, such as computing resource 224. Hypervisor 224-4 may present a virtual operating platform to the guest operating systems, and may manage the execution of the guest operating systems. Multiple instances of a variety of operating systems may share virtualized hardware resources.

Network 230 includes one or more wired and/or wireless networks. For example, network 230 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
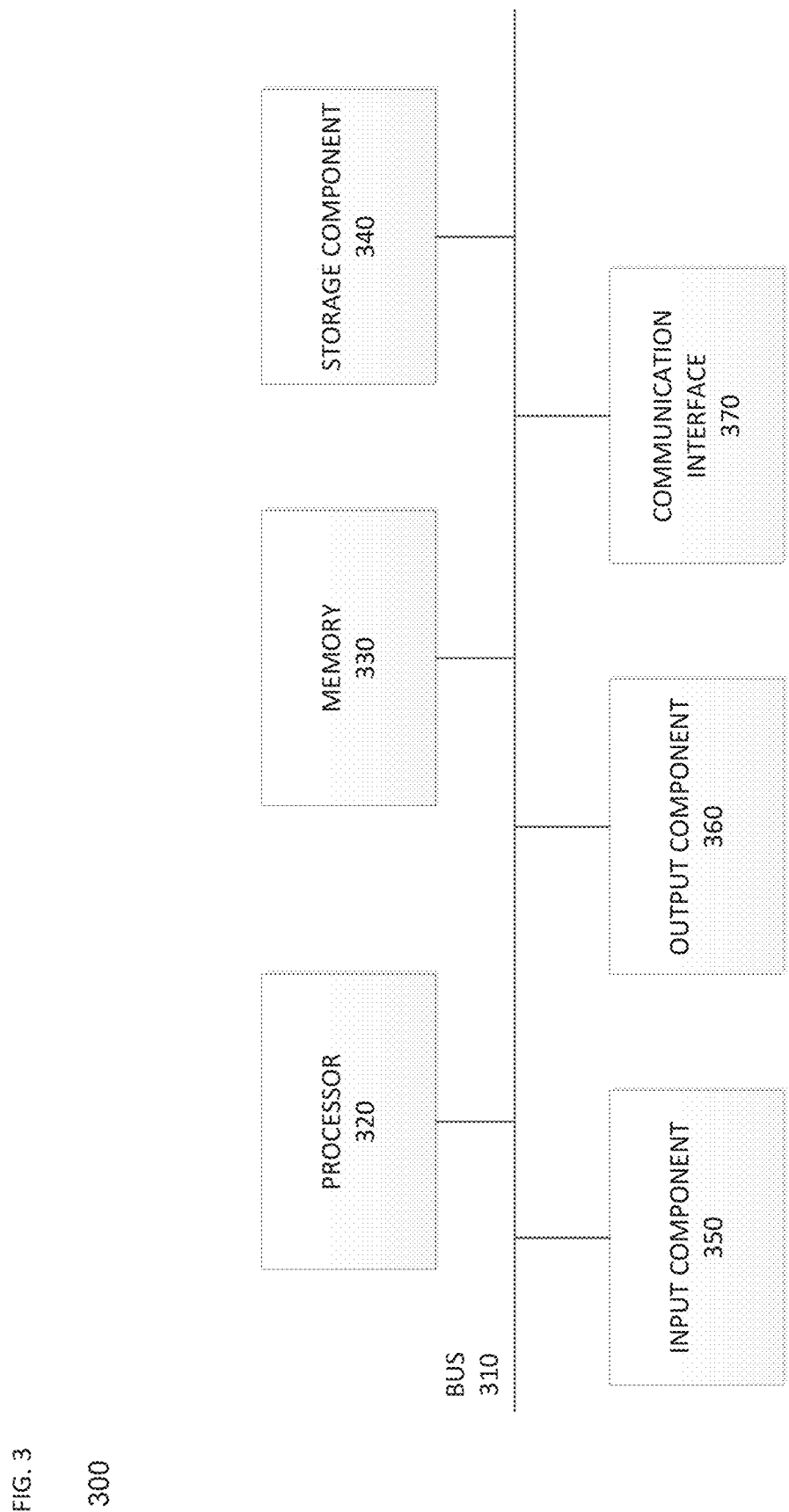
FIG. 3 is a diagram of example components of one or more devices of FIG. 2.

FIG. 3 is a diagram of example components of a device 300. Device 300 may correspond to user device 210 and/or platform 220. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

FIG. 4 is a flow chart of an example process 400 for determining diagnosis information using a reinforcement learning model. In some implementations, one or more process blocks of FIG. 4 may be performed by platform 220. In some implementations, one or more process blocks of FIG. 4 may be performed by another device or a group of devices separate from or including platform 220, such as user device 210.

As shown in FIG. 4, process 400 may include receiving, by a device, medical information associated with a user (block 410).

For example, the platform 220 may receive medical information associated with a user, such as EMR data, EHR data, and/or other types of formatted medical data. The medical information may identify disease history, symptoms, treatment history, biological information, drug information, and/or the like.

The platform 220 may receive the medical information and use a technique to identify particular information, such as a named entity recognition (NER) technique, a semantic role labelling technique, data mining technique, parsing technique, and/or the like.

As further shown in FIG. 4, process 400 may include determining, by the device, inquiry information based on the medical information (block 420).

The platform 220 may determine, based on the medical information, potential questions to be provided to a doctor, medical professional, etc. in order to ascertain additional information relevant to an ultimate diagnosis. As examples, the questions may be questions regarding a current illness, previous illness, medicinal history, test results, etc.

The platform 220 may determine a set of potential questions, and determine importance scores of the respective potential questions. As an example, a highly relevant or probative questions might be associated with a high importance score whereas a less relevant or less probative question might be associated with a lower importance score.

The platform 220 may determine the set of importance scores using a reinforcement learning technique. For example, the platform 220 may train a reward function of a reinforcement learning model using EMR, EHR, knowledge base data, rule data, and/or the like.

As further shown in FIG. 4, process 400 may include determining whether the inquiry information satisfies a threshold score (block 430). The platform 220 may determine whether a potential question includes an importance score that satisfies a threshold score. In this way, the platform 220 may determine a particular question to provide to a doctor, medical professional, etc.

As further shown in FIG. 4, if the inquiry information does not satisfy the threshold score (block 430—NO), then process 400 may include returning to block 420. In this case, the platform 220 may determine another potential question to provide.

As further shown in FIG. 4, if the inquiry information satisfies the threshold score (block 430—YES), then process 400 may include providing, by the device, the inquiry information to permit response information to be received (block 440).

The platform 220 may provide the inquiry information (e.g., a question, a request for information, etc.) to another device or an output component to permit response information to be received.

As further shown in FIG. 4, process 400 may include receiving, by the device, the response information based on providing the inquiry information (block 450).

The platform 220 may receive, from another device (e.g., which may have received an input from a doctor, medical professional, etc.), the response information based on the inquiry information.

As further shown in FIG. 4, process 400 may include determining, by the device, diagnosis information based on the medical information and the response information using a machine learning model (block 460).

The platform 220 may determine diagnosis information, such as information that identifies a diagnosis, a treatment option, a drug to be prescribed, and/or the like, based on the medical information and the response information.

The platform 220 may determine the diagnosis information using a model, such as a recurrent neural network (RNN) technique, a convolutional neural network (CNN) technique, a support vector machine (SVM), and/or the like.

As further shown in FIG. 4, process 400 may include providing, by the device, the diagnosis information to a set of devices via a network (block 470).

The platform 220 may provide the diagnosis information to a set of other devices via a network in real time. In some implementations, the platform 220 may provide the diagnosis information in a standardized format to permit various databases and records to be updated based on the diagnosis information.

The platform 220 may provide the diagnosis information in a standardized format to a set of devices via a network in real time. The platform 220 may standardize the diagnosis information using a standardization technique, such that the set of devices may each utilize the standardized diagnosis information.

The platform 220 may collect medical information, and convert and consolidate the medical information from various physicians and medical providers into a standardized format. Further, the platform 220 may generate diagnosis information in association with a standardized format. The platform 220 may store the standardized medical information and/or diagnosis information in a set of network-based storage devices (e.g., platform 220), and generate messages notifying health care providers, doctors, medical personnel, patients, etc. whenever the medical information and/or diagnosis information is generated, updated, etc.

Further, the platform 220 may provide the diagnosis information to the set of devices in real time (e.g., substantially concurrently with the generation of the diagnosis information) to permit the set of devices to update and/or utilize the diagnosis information in real time. In this way, various users of the set of devices may have immediate access to up-to-date diagnosis information.

In this way, and as compared to non-standardized medical information associated with different medical providers, some implementations herein permit standardized medical information and/or diagnosis information to be generated and provided to multiple different devices in real time, thereby allowing different users to share medical information and/or diagnosis information.

Further still, and in this way, some implementations herein permit complete and accurate medical information and/or diagnosis information to be provided in real time. As compared to situations where multiple disparate medical personnel have incomplete or inaccurate medical or diagnosis information, some implementations herein permit complete and accurate medical and diagnosis information to be disseminated and readily-shared between medical personnel.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method comprising:
   receiving, by a device, medical information associated with a user;
   training, by the device, a reinforcement learning model using at least one of electronic medical record (EMR) data and electronic health record (EHR) data to maximize a reward function that scores importance of a plurality of potential questions;
   determining, by the device, questions to ask the user based on the medical information associated with the user and the trained reinforcement learning model;
   providing, by the device, the questions to a doctor to permit response information to be received;
   receiving, by the device, the response information based on the questions;
   determining, by the device, diagnosis information based on the medical information and the response information using a machine learning model; and
   providing, by the device, the diagnosis information in a standardized format to a set of devices via a network in real time,
   wherein the determining questions comprises determining, by the device, whether an importance score of a potential question of the plurality of potential questions is greater than a threshold score, wherein the importance score is determined using at least a risk of death associated with question uncertainty, reinforcement learning, and at least a risk of death associated with question uncertainty, reinforcement learning, and at least one of: how relevant a potential question is, or how probative a potential question is; and
   when the importance score is greater than the threshold score, determining the potential question as one of the questions to ask the user.

2. The method of claim 1, further comprising:
   performing a named entity recognition technique using the medical information; and
   wherein determining the diagnosis information comprises determining the diagnosis information based on the named entity recognition technique.

3. The method of claim 1, further comprising:
   performing a semantic role labelling technique using the medical information; and
   wherein determining the diagnosis information comprises determining the diagnosis information based on the semantic role labelling technique.

4. The method of claim 1, wherein the reinforcement learning model has been trained by:
   determining, based on the medical information, a set of potential questions;
   determining respective importance scores associated with the set of potential questions that indicate the importance of the associated potential questions;
   inputting the respective scores and the set of potential questions into the reinforcement learning model,
   wherein the reward function maximizes the importance score.

5. The method of claim 1, wherein determining the diagnosis information comprises determining the diagnosis information using at least one of a recurrent neural network (RNN), a convolutional neural network (CNN), and support vector machine (SVM).

6. The method of claim 1, wherein the determining the questions to ask the user comprises:

determining a set of importance scores corresponding to the plurality of potential questions based on the medical information associated with the user and the trained reinforcement learning model that has been trained using at least one of electronic medical record (EMR) data and electronic health record (EHR) data to maximize the reward function that scores the importance of the plurality of potential questions.

7. A device comprising:
at least one memory configured to store program code;
at least one processor configured to read the program code and operate as instructed by the program code, the program code comprising:
first receiving code configured to cause the at least one processor to receive medical information associated with a user;
first training code configured to cause the at least one processor to train a reinforcement learning model using at least one of electronic medical record (EMR) data and electronic health record (EHR) data to maximize a reward function that scores importance of a plurality of potential questions;
first determining code configured to cause the at least one processor to determine questions to ask the user based on the medical information associated with the user and the trained reinforcement learning model;
providing code configured to cause the at least one processor to provide the questions to a doctor to permit response information to be received;
second receiving code configured to cause the at least one processor to receive the response information based on the questions;
second determining code configured to cause the at least one processor to determine diagnosis information based on the medical information and the response information using a machine learning model; and
providing code configured to cause the at least one processor to provide the diagnosis information in a standardized format to a set of devices via a network in real time,
wherein the first determining code is configured to cause the at least one processor to determine whether an importance score of a potential question of the plurality of potential questions is greater than a threshold score, wherein the importance score is determined using at least a risk of death associated with question uncertainty, reinforcement learning, and at least one of: how relevant a potential question is, or how probative a potential question is; and
when the importance score is greater than the threshold score, determine the potential question as one of the questions to ask the user.

8. The device of claim 7, further comprising:
performing code configured to cause the at least one processor to perform a named entity recognition technique using the medical information; and
wherein the second determining code is configured to cause the at least one processor to determine the diagnosis information based on performing the named entity recognition technique.

9. The device of claim 7, further comprising:
performing code configured to cause the at least one processor to perform a semantic role labelling technique using the medical information; and wherein the second determining code is configured to cause the at least one processor determine the diagnosis information based on the semantic role labelling technique.

10. The device of claim 7, wherein the reinforcement learning model has been trained by:
determining, based on the medical information, a set of potential questions;
determining respective importance scores associated with the set of potential questions that indicate the importance of the associated potential questions;
inputting the respective scores and the set of potential questions into the reinforcement learning model,
wherein the reward function maximizes the importance score.

11. The device of claim 7, wherein the second determining code is configured to cause the at least one processor to determine the diagnosis information comprises using at least one of a recurrent neural network (RNN), a convolutional neural network (CNN), and support vector machine (SVM).

12. The device of claim 7, wherein to determine the questions to ask the user, the first determining code is configured to cause the at least one processor to at least:
determine a set of importance scores corresponding to the plurality of potential questions based on the medical information associated with the user and the trained reinforcement learning model that has been trained using at least one of electronic medical record (EMR) data and electronic health record (EHR) data to maximize the reward function that scores the importance of the plurality of potential questions.

13. A non-transitory computer-readable medium storing instructions, the instructions comprising: one or more instructions that, when executed by one or more processors of a device, cause the one or more processors to at least:
receive medical information associated with a user;
training a reinforcement learning model using at least one of electronic medical record (EMR) data and electronic health record (EHR) data to maximize a reward function that scores importance of a plurality of potential questions;
determine questions to ask the user based on the medical information associated with the user and the trained reinforcement learning model that has been trained;
provide the questions to a doctor to permit response information to be received;
receive the response information based on the questions;
determine diagnosis information based on the medical information and the response information using a machine learning model; and
provide the diagnosis information in a standardized format to a set of devices via a network in real time,
wherein the one or more processors are configured to determine the questions to ask the user by determining whether an importance score of a potential question of the plurality of potential questions is greater than a threshold score, wherein the importance score is determined using at least a risk of death associated with question uncertainty, reinforcement learning, and at least one of: how relevant a potential question is, or how probative a potential question is; and
when the importance score is greater than the threshold score, determining the potential question as one of the questions to ask the user.

14. The non-transitory computer-readable medium of claim 13, wherein the one or more instructions cause the one or more processors to:

perform named entity recognition technique using the medical information; and
wherein the one or more instructions, that cause the one or more processors to determine the diagnosis information, cause the one or more processors to determine the diagnosis information based on the named entity recognition technique.

15. The non-transitory computer-readable medium of claim 13, wherein the one or more instructions cause the one or more processors to:
perform a semantic role labelling technique using the medical information; and
wherein the one or more instructions, that cause the one or more processors to determine the diagnosis information, cause the one or more processors to determine the diagnosis information based on the semantic role labelling technique.

16. The non-transitory computer-readable medium of claim 13, wherein the reinforcement learning model has been trained by:
determining, based on the medical information, a set of potential questions;
determining respective importance scores associated with the set of potential questions that indicate the importance of the associated potential questions;
inputting the respective scores and the set of potential questions into the reinforcement learning model,
wherein the reward function maximizes the importance score.

17. The non-transitory computer-readable medium of claim 13, wherein to determine the questions to ask the user, the one or more instructions that, when executed by one or more processors of a device, cause the one or more processors to at least:
determining a set of importance scores corresponding to the plurality of potential questions based on the medical information associated with the user and the trained reinforcement learning model that has been trained using at least one of electronic medical record (EMR) data and electronic health record (EHR) data to maximize the reward function that scores the importance of the plurality of potential questions.

\* \* \* \* \*